US006775867B1

(12) United States Patent
Kuphal et al.

(10) Patent No.: US 6,775,867 B1
(45) Date of Patent: Aug. 17, 2004

(54) UROLOGICAL PATIENT POSITIONING TABLE

(75) Inventors: Wilko Kuphal, Rueckersdorf (DE); Walter Polster, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 20 days.

(21) Appl. No.: 09/710,902

(22) Filed: Nov. 14, 2000

(30) Foreign Application Priority Data

Nov. 26, 1999 (DE) .......................................... 199 57 129

(51) Int. Cl.[7] .......................... A61G 13/04; A61G 13/06; H05G 1/02
(52) U.S. Cl. ............................... 5/601; 5/610; 378/196; 378/209
(58) Field of Search ............................ 5/601, 611, 610, 5/600; 378/196, 209

(56) References Cited

U.S. PATENT DOCUMENTS

| 3,302,022 | A | * | 1/1967 | Brenmer et al. ................ 5/601 |
| 4,287,422 | A | * | 9/1981 | Kuphal et al. .............. 378/209 |
| 4,960,271 | A | | 10/1990 | Sebring |
| 5,013,018 | A | * | 5/1991 | Sicek et al. ..................... 5/601 |
| 5,131,105 | A | * | 7/1992 | Harrawood et al. ........... 5/610 |
| 6,244,745 | B1 | * | 6/2001 | Mattern ...................... 378/209 |
| 6,298,506 | B1 | * | 10/2001 | Heinold et al. ................ 5/601 |

FOREIGN PATENT DOCUMENTS

| DE | OS 197 21 537 | 11/1998 |
| DE | PS 42 10 866 | 3/1999 |

* cited by examiner

Primary Examiner—Alexander Grosz
(74) Attorney, Agent, or Firm—Schiff Hardin LLP

(57) ABSTRACT

A urological patient positioning table has a patient positioning plate with a head end and a foot end, and has a lifting column connected to the patient positioning plate. The lifting column is arranged at the head end of the patient positioning plate laterally next to the patient positioning plate.

9 Claims, 3 Drawing Sheets

UROLOGICAL PATIENT POSITIONING TABLE

BACKGROUND OF THE INVENTION

1. Field of the Invention

The present invention is directed to a urological patient positioning table of the type having a patient positioning plate that with a head end and a foot end, and having a lifting column connected to the patient positioning plate.

2. Description of the Prior Art

Patient positioning tables of this type are utilized for urological examinations of patients as well as for surgical interventions in urogenital regions of patients. Urological patent positioning tables are distinguished by relatively short patient positioning plates having lengths of around 1 m to 1.50 m that suffice for suitably supporting the patient. As a rule, the patient positioning plate of a urological patient positioning table has an x-ray transparent region in order, in combination with an x-ray system, to be able to implement radiological examinations of urogenital regions of patients, or surgical interventions in urogenital regions, under x-ray supervision. In order to be able to examine a patient not only in a prone position but also in a seated or standing posture, the patient positioning plate of a urological patient positioning table is pivotable around an axis that usually proceeds horizontally at a right angle relative to the longitudinal axis of the patient positioning plate.

Such a patient positioning table is disclosed, for example, in German OS 42 10 866. The patient positioning table has a patient positioning plate with a foot end and a head end that is connected to a lifting column arranged at the foot end of the patient positioning plate. With a swivel mechanism that is likewise arranged at the foot end of the patient positioning plate, which is the support side of the urogenital region of a patient, the patient positioning plate is pivotable relative to the lifting column around a horizontal axis. A disadvantage of this patient positioning table is that the urogenital region of a patient seated on the patient positioning table is only partly accessible to a urologist examining the patient. The lifting column that is disposed laterally at the foot end of the patient positioning plate can act as an impediment to free access to the urogenital region of the patient, and the swivel device arranged at the foot end under the patient positioning plate for pivoting the patent positioning plate around the horizontally proceeding axis can act as an impediment to the legs of a urologist working at the patient positioning table in a sitting position.

German OS 197 21 537 discloses another patient positioning table of the type initially described having a lifting column and a patient positioning plate that is pivotable around a horizontal proceeding axis with a swivel device arranged at the foot end of the patient positioning plate. With this patient positioning table, the accessibility to the patient borne on the patient positioning plate is in fact improved as a result of the lifting column being arranged under the patient positioning plate; nonetheless, impediments for a urologist examining a patient borne on the patient positioning plate can occur due to the lifting column being arranged at the examination side for the urogenital region and the swivel device being connected to the lifting column.

SUMMARY OF THE INVENTION

Then object of the present invention is to implement a urological patient positioning table of the type initially described such that a patient placed on the patient positioning plate is freely accessible laterally and frontally in the urogenital region.

This object is inventively achieved in a urological patient positioning table with a patient positioning plate that has a head end and a foot end and that has a carrying arm for the patient positioning plate connected to a lifting column, with the lifting column and the carrying arm are arranged at the head end of the patient positioning plate to the side next to the patient positioning plate. As a result of this arrangement of the lifting column, access to the urogenital region (placed at the foot end of the patient plate) of a patient positioned on the patient positioning plate in a lying position is not impeded by the lifting column of the patient positioning table, so that the urogenital region of a patient on the patient positioning plate is freely accessible at both sides as well as frontally.

U.S. Pat. No. 4,960,271 discloses a patient positioning table provided for surgery, catheterization, angiography or traumatology that has a carrying arm connected to a support column. The carrying arm has a fastening mechanism, so that a patient positioning plate can be optionally secured to the carrying arm projecting away from the carrying arm to the left or right.

In a preferred embodiment of the invention the patient positioning plate of the urological patient positioning table is pivotable around a substantially horizontal axis, the horizontal axis being arranged at the head end of the patient positioning plate and proceeding substantially at a right angle relative to the longitudinal axis of the plate. The arrangement of the horizontal axis of the patient positioning table at the head end of the patient positioning plate makes it possible to keep the foot end of the patient positioning plate, which represents the treatment side of a patient in a lying position on the patient positioning table, free of any and all component, i.e. free of a swivel device containing the axis. Since components of a swivel device are not located under the patient positioning plate at the foot end of the patient positioning plate there are, moreover, no impediments for the legs of a urologist projecting under the patient positioning plate when the urologist examines a patient when seated.

In another embodiment of the invention, the patient positioning plate can be swivelled around the horizontal axis—proceeding from a horizontal initial position—in an angular range from a +90° raised position to a −20° lowered position of the foot end of the patient positioning plate. The invention thereby allows repositioning the patient for sitting or standing examinations, i.e. positioning the patient with his/her head at the actual foot end and the buttocks at the actual head end of the patient positioning plate. To this end, a seat and a bench can be attached to the head end of the patient positioning plate. An examination of a patient in a sitting or standing posture would in fact also be possible at the patient positioning plate if the patient positioning plate were pivoted around the horizontally proceeding axis by −90°, i.e. lowered position of the foot end of the patient positioning plate, from its horizontal initial position. In this case, however, a relatively large, vertical adjustment motion of the horizontally proceeding axis and of the patient positioning plate would have to ensue in order, given the required swivel event, to avoid contact of the patent positioning plate with the floor of the room containing the patient positioning table; for this reason, the first version is preferred.

In another version of the invention, the patient positioning plate has an x-ray transparent region in order to implement radiological examinations of the urogenital region of a patient at the patient positioning table. The patient positioning plate can be completely formed of a material that is transparent to x-rays.

In an embodiment of the invention, the patient positioning table has a stand for accepting at least one apparatus part, and an x-ray source and an x-ray receiver can be attached to the stand in one version of the invention. Preferably, the x-ray source to and the x-ray receiver, which can be an x-ray image intensifier, an aSi flat image detector or an x-ray film, are arranged at the stand lying opposite one another so that the central ray of an x-ray beam emanating from the x-ray source is approximately try centrally incident on the x-ray receiver.

In a preferred embodiment of the invention the stand has at least two sections directed substantially parallel to the longitudinal axis of the patient positioning plate, which has an upper side for the patient positioning and a lower side. One section is arranged at the side of the upper side and the other section is arranged at the side of the lower side of the patient positioning plate. In a version of the invention, the x-ray source is arranged at the one section and the x-ray receiver is arranged at the other section. Independently of one another, the x-ray source and the x-ray receiver are adjustable relative to the respective section that carries them, this adjustment ensuing substantially in the direction of the longitudinal axis of the patient positioning plate and/or transversely relative to the longitudinal axis of the patient positioning plate. In another version of the invention, the adjustments of the x-ray source and of the x-ray receiver preferably ensue synchronously. These embodiments of the invention make it possible to keep the patient as well as the stand at rest during radiological examination of various body regions of the patient positioned on the patient positioning table. The risk of injuries is thereby reduced for patients who, for example, undergo surgical interventions under x-ray supervision wherein, as in endoscopic interventions during which instruments are employed, the x-ray receiver and the patient must be displaced relative to one another for the purpose of x-ray monitoring. Because the x-ray source as well as the x-ray receiver (rather than the stand) are displaced relative to the patient, the stand no longer blocks access to the patient given x-ray exposures of the urogenital region of a patient, as is usually the case given adjustable stands that must be placed next to the urogenital region for such x-ray exposures.

In a further version of the invention the patient positioning table has the carrying by part connected to the lifting column pivotable around the horizontal axis relative to the lifting column, with the patient positioning plate and the stand arranged at the carrying part. In this way, the patient positioning plate and the stand can be pivoted in common around the horizontally proceeding axis.

In further versions of the invention the patient positioning plate and/or the stand are adjustable relative to the carrying part in the direction of the longitudinal axis and/or transversely relative to the longitudinal axis of the patient positioning plate, so that versatile possibilities for placing a patient relative to the x-ray source and the x-ray receiver are achieved.

DESCRIPTION OF THE PREFERRED EMBODIMENTS

Figure 1:
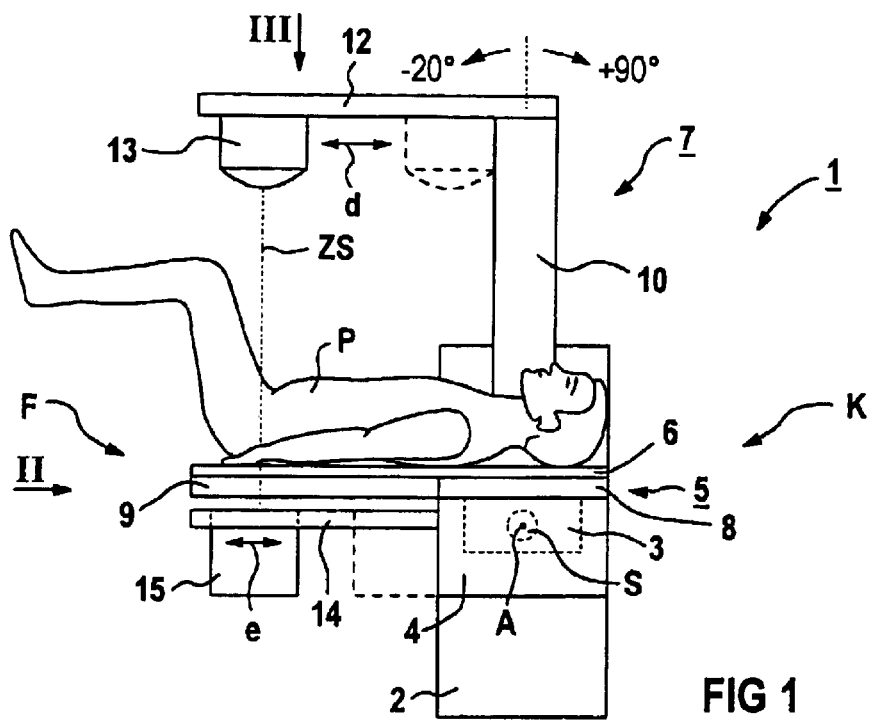
FIG. 1 is a side view of an inventive patient positioning table.
Figure 2:
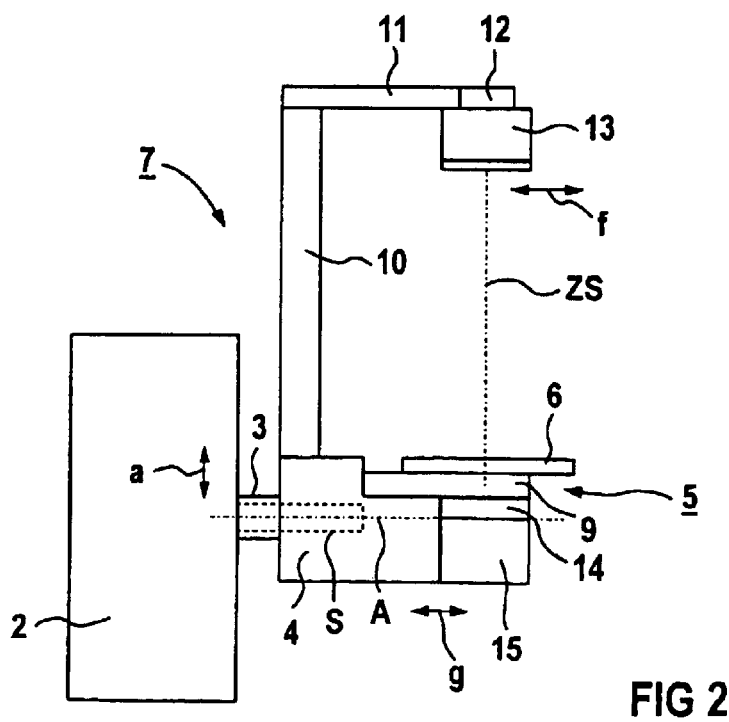
FIG. 2 is a view of the patient positioning table of FIG. 1 in the direction of the arrow II in FIG. 1.
Figure 3:
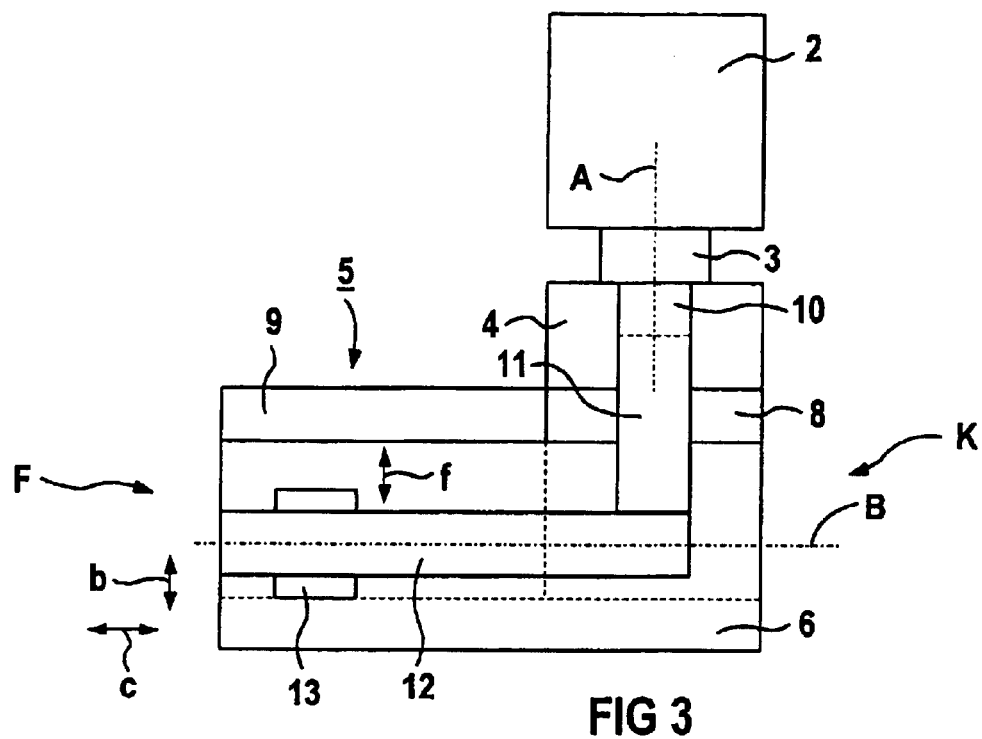
FIG. 3 is a view of the patient positioning table of FIG. 1 in the direction of the arrow III of FIG. 1.

In the exemplary embodiment, the inventive patient positioning table 1 shown in various views in FIGS. 1 through 5 has a lifting column 2 arranged on the floor of a room, at which a carrying arm 3 is seated so as to be vertically adjustable in the directions of the double arrow a. A carrier part 4 is arranged at the carrying arm 3, this carrier part 4 being mounted with a swivel device S so as to be pivotable relative to the lifting column 2 and the carrying arm 3 around substantially horizontally proceeding axis A of the patient positioning table 1. A holding mechanism 5 for a patient positioning plate 6, having a longitudinal axis B, and for a stand 7 is secured to the carrier part 4.

The holding device 5 for the patient positioning plate 6 has two sections 8 and 9. The first section 8 in the exemplary embodiment is composed of a material that is not transparent for x-rays and the second section 9 is fashioned of a material transparent for x-rays. The patient positioning plate 6 itself is completely fashioned of a material transparent x-radiation and, relative to the holding device 5, is seated to be adjustable in the directions of the double arrows b and c transversely and longitudinally relative to the horizontal axis A. The bearing of the patient positioning plate 6 can, for example, ensue with rails (not shown).

The stand 7 is formed of two parts. The first part of the stand 7 in the present embodiment has a column secured to the carrier part 4 that is vertically directed in the initial position of the carrier part 4 shown in FIG. 1, has a section 11 arranged at a right angle thereto and horizontally directed parallel to the axis A, and a section 12 arranged at a right angle thereto that is directed substantially parallel to the longitudinal axis B of the patent positioning plate 6, so that the first part of the stand 7 forms an angled carrying arm. In the exemplary embodiment, an x-ray source 13 is arranged at the section 12, this being adjustably seated (in a way not shown in greater detail) at the section 12 along the longitudinal axis B in the directions of the double arrow d and transversely relative to the longitudinal axis B of the patient positioning plate 6 in the directions of the double arrow f.

The second part of the stand 7 is arranged at the carrier part 4 under the patient positioning plate 5 and has a section 14 directed substantially parallel to the longitudinal axis B of the patient positioning plate 6. In the exemplary embodiment, an x-ray image intensifier 15 is seated (in a way not shown in greater detail) at the section 14 so as to be adjustable along the longitudinal axis B in the directions of the double arrow e and transversely relative to the longitudinal axis B of the patient positioning plate 6 in the directions of the double arrow g. Instead of the x-ray image intensifier 15, an aSi flat image detector or an x-ray film accepted in a cassette or a cassette carriage can also be employed as the x-ray receiver.

The adjustment of the x-ray source 13 at the section 12 as well as the adjustment of the x-ray image intensifier 15 at the section 14 preferably ensue with electric motors (not shown in greater detail) that are preferably synchronously driven by a control arrangement (likewise not shown in greater detail) in the form of a known control computer. The x-ray source 13 and the x-ray image intensifier 15, however, alternatively can be adjusted independently of one another, whereby the x-ray source 13 and the x-ray image intensifier 15 can be aligned relative to one another with the control, which knows the positions thereof, so that the central ray CS of an x-ray beam emanating from the x-ray source 13 in x-ray exposures is approximately centrally incident on the input luminescent screen of the x-ray image intensifier 15.

The adjustment of the x-ray source 13 and of the x-ray image intensifier 15, however, need not necessarily ensue under motor drive but can ensue manually.

FIG. 1 schematically shows the prone positioning of a patient P on the patient positioning plate 6 of the patient positioning table 1, with the head of the patient P disposed at the head end K and the urogenital region of the patient P is disposed at the foot end F of the patient positioning plate 6. Although not shown in FIG. 1, known auxiliary means for positioning the patient P such as leg or arm supports can be arranged at the patient positioning plate 6.

As can be seen from FIG. 1, as a result of the arrangement of the pivot device S containing the horizontally proceeding axis A at the head end K of the patient positioning plate 6, as well as due to the arrangement of the lifting column 4 connected to the swivel device S laterally next to the head end K of the patient positioning plate 6, the space around the foot end F of the patient positioning plate 6 on which, as already mentioned, the urogenital region of the patient P to be examined is placed, is not blocked by any components of the patient positioning table 1, and the patient positioning table is thus laterally as well as frontally freely accessible in the region of the foot end F of the patient positioning plate 6.

The x-ray source 13 and the x-ray image intensifier 15—as long as no radiological examination is ensuing—can be adjusted into standby positions, indicated with broken lines in FIG. 1. Alternatively, however, and as already mentioned, a space-saving x-ray detector, for example an aSi flat image detector or an x-ray film accepted in a cassette mechanism, can be employed instead of the x-ray image intensifier 15; these can be adjustably integrated in the section 9 of the holding device 5.

As indicated in FIG. 1, the patient positioning plate 6 arranged at the carrier part 4 can be pivoted from the horizontal initial position of the patient positioning plate 6 shown in FIG. 1 through an angular range encompassing a +90° raised position of the foot end F to a −20° lowered position of the foot end F. This pivoting takes place around the horizontally proceeding axis A, so that examinations at the patient are also possible given a pivoted patient positioning plate 6.

Figure 4:
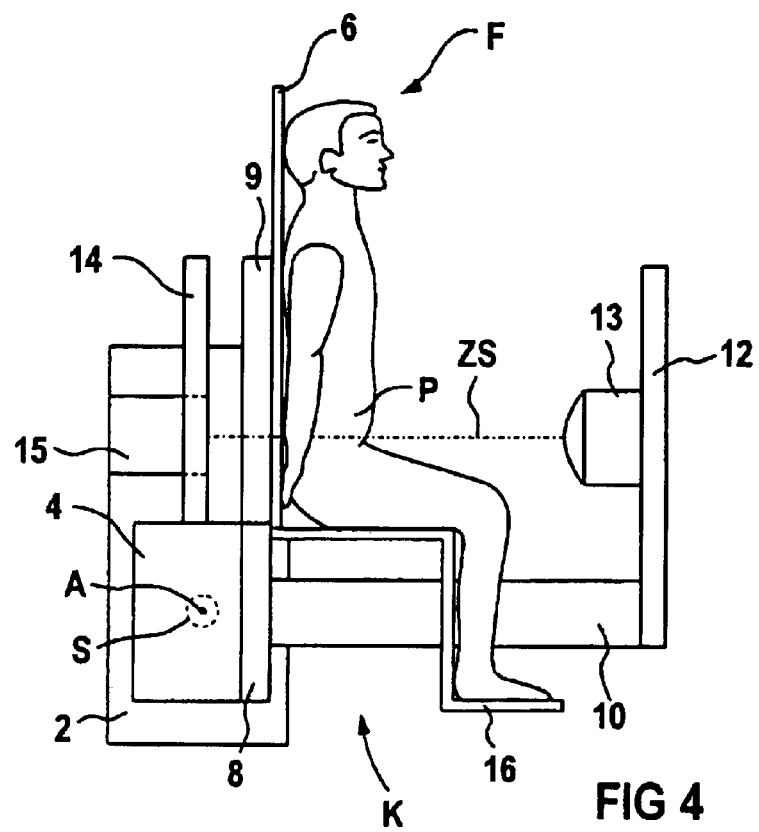
FIG. 4 shows the patient positioning table of FIG. 1 with a pivoted patient positioning plate and pivoted stand for examining a patient in a seated position.
Figure 5:
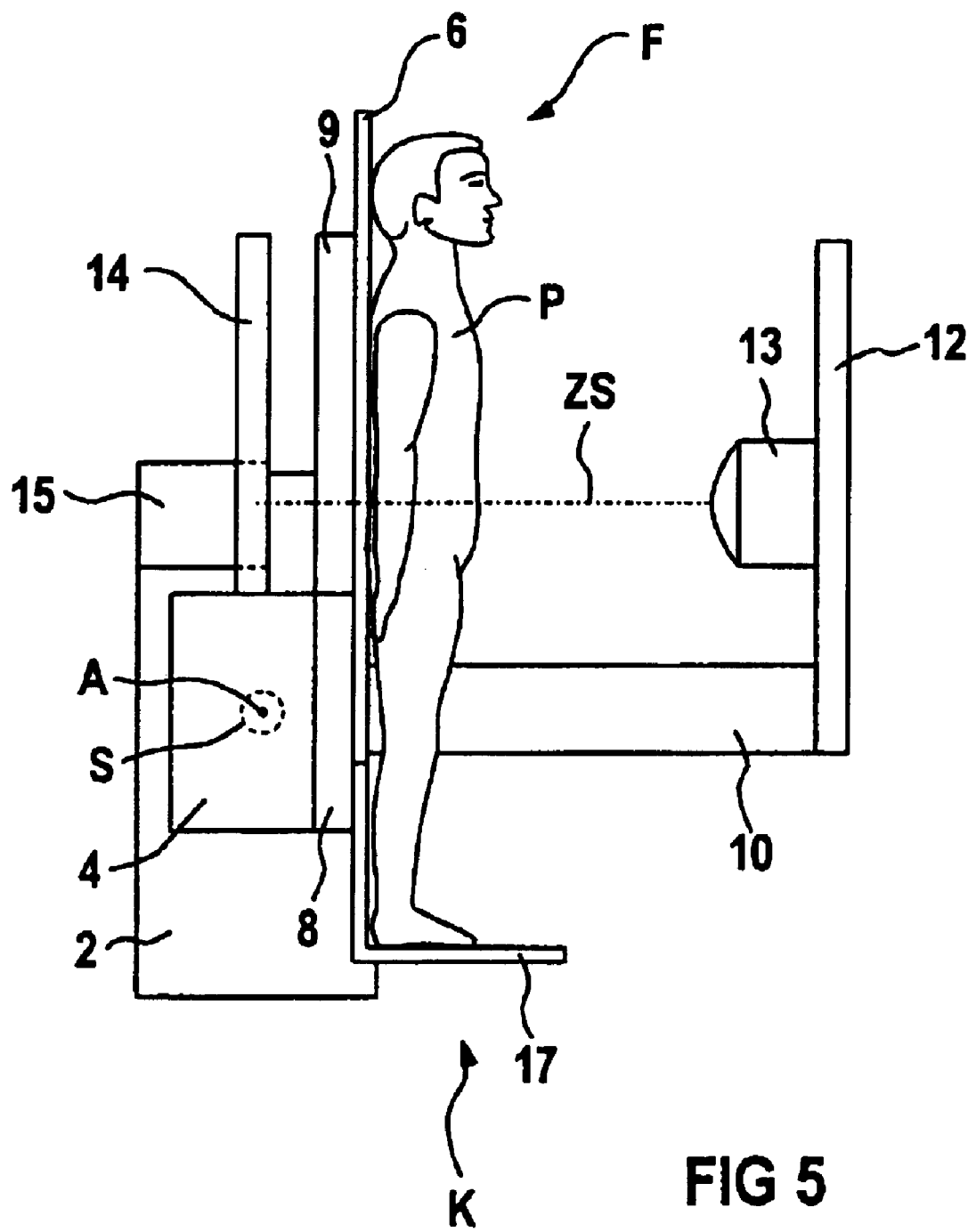
FIG. 5 shows the patient positioning table of FIG. 1 with pivoted patient positioning plate and pivoted stand for examining a patient in a standing posture.

For examining the patient P in a sitting or standing position, as shown in FIGS. 4 and 5, the carrier part 4, and thus the patient positioning plate 6 and the stand 7, are pivoted either manually or under motor drive by +90° raised position of the foot end F around the horizontally proceeding axis A. The patient positioning table 1 shown in the exemplary embodiment allows repositioning of the patient P for sifting or standing examinations, i.e. placing the buttocks at the actual head end K and the head at the actual foot end F of the patient positioning plate. Dependent on the size of the patient P to be examined, the carrier part 4 can be adjusted vertically relative to the lifting column 2 and/or the patient positioning plate 6 can be adjusted relative to the holding device 5, and thus relative to the carrier part 4, so that urogenital region of the patient P to be radiologically examined is located in the x-ray transparent section 9 of the holding device 5. For examining the patient P in a sitting or standing posture, a seat 16 and a bench 17 on which the patient P can be placed can be attached in a known way to the head part K of the patient positioning plate 6.

In the exemplary embodiment, the x-ray source 13 and the x-ray image intensifier 15 are adjustably attached to the stand 7. In another embodiment of the invention, which is not shown in greater detail, the stand 7 also can be adjustable relative to the carrier part 4 in the direction of the longitudinal axis B of the patient positioning plate 6 and/or transversely to the longitudinal axis B of the patient positioning plate 6, for this purpose given the employment of the stand 7 described for the exemplary embodiment, the two parts of the stand 7 must be adjustable relative to the carrier part 4. When the stand forms a unit, then this unit is to be adjustably seated only relative to the carrier part 4.

Moreover, the stand utilized at the patient positioning plate need not necessarily have an angled carrying arm. The stand can also be fashioned C-shaped in a known to way.

In the exemplary embodiment, further, the carrier part 4 together with the patient positioning plate 6 and the stand 7 are pivotable around the horizontally proceeding axis A so that a +90° raised position or a −20° lowered position of the foot end F of the patient positioning plate 6 can be reached proceeding from its horizontal initial position. In another embodiment of the invention, the carrier part 4 together with the patient positioning plate 6 and the stand 7 can be implemented to be pivotable around the horizontally proceeding axis A in an angular range from a −90° lowered position through a +20° raised position of the foot end F. This embodiment of the invention, however, requires a relatively large implementation of the lifting column in order to be able to vertically adjust the carrier part 4 such that, given pivot events around the horizontally proceeding axis A form −90° lowered position of the foot end F, contact of the patient positioning plate 6 with the floor of the room accepting the patient positioning table 1 is avoided.

Although modifications and changes may be suggested by those skilled in the art, it is the intention of the inventors to embody within the patent warranted hereon all changes and modifications as reasonably and properly come within the scope of their contribution to to the art.

What is claimed is:

1. A urological patient positioning table comprising:
   a patient positioning plate having a head end and a foot end with a longitudinal axis proceeding therebetween, and an upper side and a lower side;
   a lifting column;
   a carrying arm connecting said positioning plate to said lifting column;
   said lifting column and said carrying arm being disposed at said head end of said positioning plate laterally next to said positioning plate;
   a stand comprising a first section disposed next to said upper side of said positioning plate and a second section disposed next to said lower side of said positioning plate, said second section being substantially parallel to said longitudinal axis of said positioning plate; and
   a first apparatus part mounted at said first section of said stand and a second apparatus part mounted at said second section of said stand, said first apparatus part being adjustable in position relative to said first section and said second apparatus part being adjustable in position relative to said second section, said first apparatus part and said second apparatus part each being adjustable in at least one of a first direction along said longitudinal axis and a second direction transverse to said longitudinal axis.

2. A urological patient positioning table as claimed in claim 1 wherein said positioning plate has a longitudinal axis and wherein said positioning plate is mounted to said carrying arm for rotation around a horizontal axis, said horizontal axis being disposed at said head end of said positioning plate and proceeding substantially at a right angle relative to said longitudinal axis.

3. A urological patient positioning table as claimed in claim 2 wherein said positioning plate is mounted to said carrying arm for rotation around said horizontal axis, out of a horizontal initial position, through an angular range from a +90° raised position of said foot end through a −20° lowered position of said foot end.

4. A urological patient positioning table as claimed in claim 1 wherein said patient positioning plate has a region that is transparent to x-rays.

5. A urological patient positioning table as claimed in claim 1 wherein said first apparatus part and said second apparatus part are synchronously adjustable.

6. A urological patient positioning table as claimed in claim 1 comprising a carrier part connected to said lifting column and being rotatable relative to said lifting column around a horizontal axis, said positioning plate and said stand being mounted at said carrier part, and said carrier part being attached to said carrying arm.

7. A urological patient positioning table as claimed in claim 6 wherein said processing plate is adjustable relative to said carrier part in at least one direction selected from the group consisting of a first direction along said longitudinal axis and second direction transverse to said longitudinal axis.

8. A urological patient positioning table as claimed in claim 6 wherein said stand is adjustable relative to said carrier part in a direction selected from the group consisting of a first direction along said longitudinal axis and a second direction transversely to said longitudinal axis.

9. A urological patient positioning table as claimed in claim 1 wherein said first apparatus part is an x-ray source and said second apparatus part is an x-ray receiver.

* * * * *